United States Patent [19]

Borgers et al.

[11] Patent Number: 4,795,456
[45] Date of Patent: Jan. 3, 1989

[54] STRETCHABLE DIAPER TAB

[75] Inventors: Leo Borgers, Kasterlee; Paul J. Dhondt, Vosselaar, both of Belgium

[73] Assignee: Avery International Corporation, Pasadena, Calif.

[21] Appl. No.: 106,937

[22] Filed: Oct. 8, 1987

Related U.S. Application Data

[63] Continuation of Ser. No. 840,429, Mar. 14, 1986, abandoned.

[51] Int. Cl.⁴ .............................................. A61F 13/16
[52] U.S. Cl. .................................... 604/390; 604/389
[58] Field of Search ................................ 604/389–391, 604/385.1

[56] References Cited

U.S. PATENT DOCUMENTS

| | | | |
|---|---|---|---|
| 3,833,456 | 9/1974 | Reed et al. | 604/390 |
| 3,999,546 | 12/1976 | Feldman et al. | 604/390 |
| 4,020,842 | 5/1977 | Richman et al. | 604/390 |
| 4,043,340 | 8/1977 | Cepuritis | 604/390 |
| 4,044,767 | 8/1977 | Tritsch | 604/390 |
| 4,050,121 | 9/1977 | Richman | 604/390 |
| 4,097,627 | 6/1978 | Nemeth et al. | 604/390 |
| 4,111,205 | 9/1978 | Nemeth | 604/390 |
| 4,168,196 | 9/1979 | Nemeth et al. | 604/390 |
| 4,178,933 | 12/1979 | Nemeth | 604/390 |
| 4,209,016 | 6/1980 | Schaar | 604/390 |
| 4,211,226 | 7/1980 | Schaar | 604/390 |
| 4,299,223 | 11/1981 | Conkrite | 604/390 |
| 4,389,212 | 6/1983 | Tritsch | 604/389 |
| 4,522,853 | 6/1985 | Szonn et al. | 604/389 |
| 4,585,450 | 4/1986 | Rosch et al. | 604/390 |
| 4,643,729 | 2/1987 | Laplanche | 604/389 |

FOREIGN PATENT DOCUMENTS 1225794  3/1971  United Kingdom.

Primary Examiner—C. Fred Rosenbaum
Assistant Examiner—Sharon Rose
Attorney, Agent, or Firm—Pearne, Gordon, McCoy & Granger

[57] ABSTRACT

A disposable diaper has tabs which are converted from a nonextensible to an extensible state by merely deploying the taps for diapering and without having to break a weakened joint to accomplish the conversion.

8 Claims, 1 Drawing Sheet

STRETCHABLE DIAPER TAB

This is a continuation of application Ser. No. 840,429, filed on Mar. 14, 1986, now abandoned.

BACKGROUND OF THE INVENTION

This invention relates to disposable diapers provided with adhesive tab fasteners, and particularly tab fasteners of the extensible type useful for diaper closure and in other applications.

Extensible diaper tabs have previously been proposed as a means to improve the fit of the diaper by utilizing the diaper tabs as elastic extensible side waistbands.

An early proposal is that of U.S. Pat. No. 3,800,796 to Jacobs. Later improvements or alternatives to the early Jacobs concept of an extensible tab include U.S. Pat. No. 4,051,853 to Egan and U.S. Pat. No. 4,066,081 to Schaar.

One problem with extensible tabs is the need to avoid premature stretching prior to initial fastening of the diaper, and particularly to stabilize (avoid stretching) the stretchable part of the tab material, so as to allow accurate placement of tabs on the diaper, even under the inertia stresses associated with the high line speeds that are necessary for economical manufacture. One approach to this problem of premature extension is shown in U.S. Pat. No. 4,389,212 to Tritsch. In this approach, a breakable "attachment portion" 40 (FIG. 3), 140 (FIG. 6), or 240 (FIG. 7) provides temporary stabilization. This "attachment portion" appears to be a weakened joint in the midsection of the tab, which joint is not completely parted until the end user fastens the diaper. Tritsch does not disclose how such a weakened joint is formed, nor how it is conditioned to resist breaking under high inertia stresses during diaper manufacture and yet part readily and conveniently when the diaper and its tabs are deployed to diaper a baby.

SUMMARY OF THE INVENTION

The present invention provides stabilizing means for preventing premature extension of an extensible diaper tab, but without reliance on use of a weakened joint which must be counted on to hold or part under stress according to the circumstances. Instead, the configuration of the tab is such that the stretchy tab material is freed to stretch only when the tab is deployed for diapering. Prior to that time, the stretchy tab material remains fastened to nonextensible means at all times before, during, and after application of the tab.

The result is a tab that is positively nonextensible until deployed for diapering but is rendered extensible by the very act of deployment and without having to rely on satisfactory breakability of a joint or other element.

BRIEF DESCRIPTION OF THE DRAWINGS

In the drawings, the thickness of the webs and coatings are greatly exaggerated and not to scale.

DETAILED DESCRIPTION OF THE DRAWINGS

Figure 1:
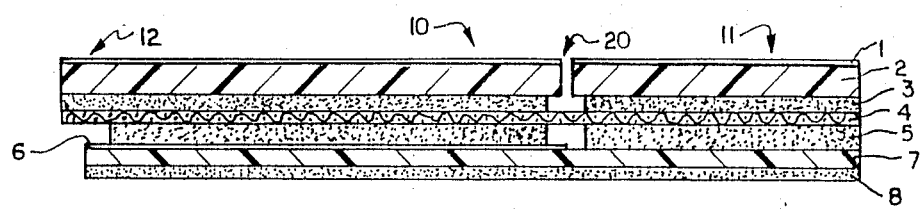
FIG. 1 is a diagrammatic transverse elevation of diaper tab stock constructed according to the invention and then cut transversely to machine direction (machine direction being into the paper) to thereby form an individual tab.

The tab seen in FIG. 1 is cut from a continuous tape of diaper tab stock, and FIG. 1 is, in effect, a diagrammatic cross-sectional view of such diaper tab stock as well as an elevational view of a single tab. The diaper tab stock consists of initially flat but flexible layers suitable to be formed in long passes along the machine direction (into or out of the paper as seen in FIG. 1) of a coating and laminating line.

These layers include an unwind release coating 1, a carrier web layer 2, a layer of pressure-sensitive adhesive 3, a layer of stretchable or extensible web 4 such as polyurethane film, a layer of pressure-sensitive adhesive 5, a liner web 7 of nonextensible material such as paper and provided along a segment on one face with suitable release means such as the release coating 6, and a layer of pressure-sensitive adhesive 8. These make up the tab stock and the individual tab 10 formed from the tab stock. At the intermediate point 20, lengthwise of each tab 10, the layer 2 along with the coating 1 is incised or slit, the layers 3 and 5 may be interrupted as shown, and the coating 6 which extends only from one end is terminated. Adhesive layers 3 and 5 have essentially no mechanical strength, and it is not necessary to interrupt them as shown, but doing so tends to improve the neatness of the deploying action, which will be described below.

Tab 10 comprises first and second terminal segments generally indicated at 11 and 12 and a central segment between segments 11 and 12 and at and surrounding intermediate point 20. It will be noted that both layers 4 and 7 are uninterrupted and that extensible layer 4 is adhered to nonextensible layer 7 at both terminal segments 11 and 12. At the first terminal segment 11, such adherence is permanent. At the second terminal segment 12, such adherence is releasable, due to the presence of the release coating 6 on the nonextensible layer 7.

Figure 2:
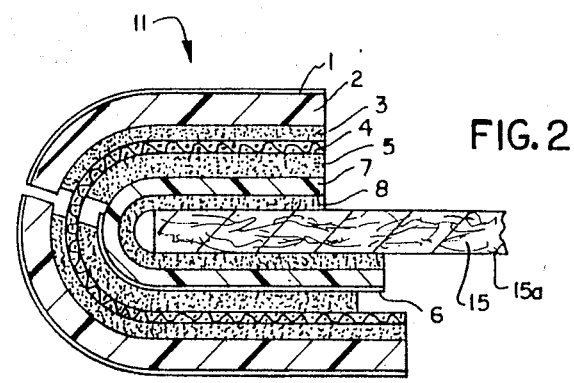
FIG. 2 is a view of the tab shown in FIG. 1, folded and fastened around one portion of a diaper by the diaper manufacturer.

FIG. 2 shows the tab of FIG. 1 placed around an edge or side margin of a diaper 15. It will be seen that layers 1-5 are relatively spaced from diaper 15. These layers 1-5 comprise outer layer means, while layers 7 and 8 comprise inner layer means which are adjacent the diaper and are permanently adhered to opposite sides of the diaper side margin at the terminal segments 11 and 12. The outer layer means 1-5 will be seen to be permanently adhered to the inner layer means 7,8 at the first terminal segment 11 and releasably adhered thereto at the second terminal segment 12. The second terminal segment 12 is on the inner side 15a of the diaper 15.

The inner layer means is nonextensible because it includes the nonextensible layer 7 and this nonextensibility is imparted to the outer layer means 1-5 so long as the latter is adhered to the inner layer means at both terminal segments 11 and 12. Thus, the tab construction is nonextensible in the conditions shown in both FIGS. 1 and 2.

Figure 3:
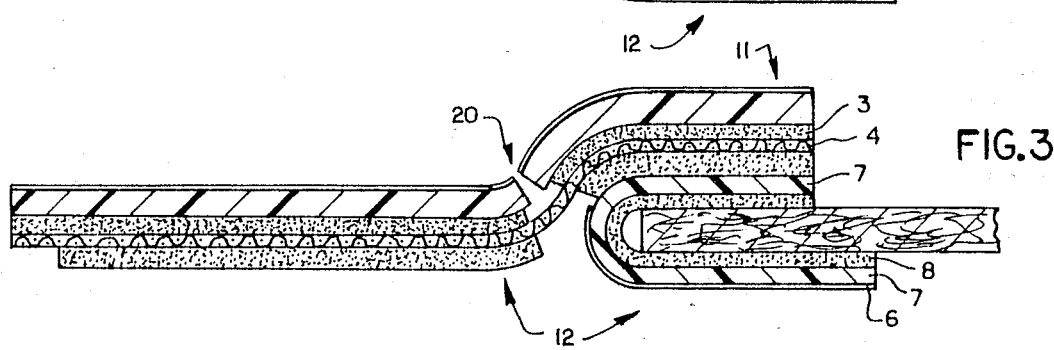
FIG. 3 is a view of the same tab now deployed for diapering.

When the tab 10 is to be deployed for diapering, the outer layer means 1-5 are released from the inner layer means 7-8 at the second terminal segment 12 to thereby expose and present the adhesive layer 5 at the second terminal end for fastening to another portion of the diaper (not shown in FIG. 3). Upon such release, the outer layer means 1-5 is no longer stablized against extension because now the only significant mechanical connection between the terminal segments of the outer layer means is the extensible layer 4. This conversion from the nonextensible to the extensible state is accomplished simply by the releasing of the outer layer means from the inner layer means at the terminal segment 12, and without having to rely on satisfactory breakability of a joint or other element.

It is desirable that extensibility be generally concentrated at the central segment that surrounds intermediate point 20 and is between terminal segments 11 and 12. It will be noted that even in the deployed condition of the tab, the terminal segments 11 and 12 remain constrained against stretching by the anchoring action of the non-extensible carrier layer 2 which remains adhered to the extensible layer 4 at the terminal segments 11 and 12.

Figure 4:
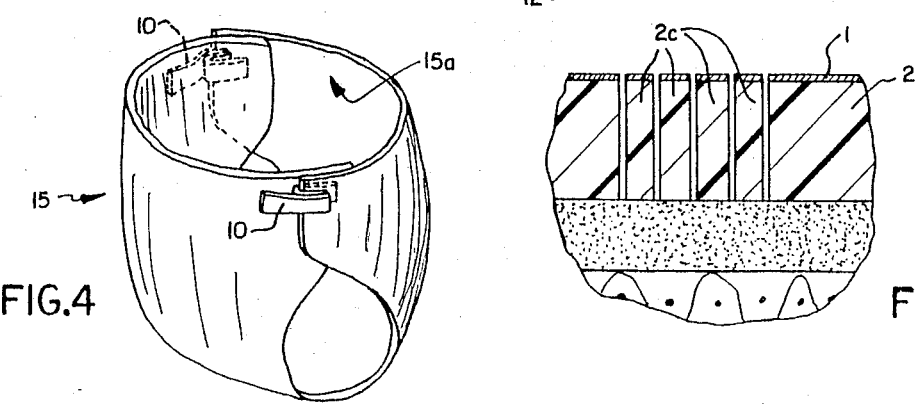
FIG. 4 is a sketch on a much smaller scale of a diaper fastened with a pair of the tabs.

FIG. 4 shows the diaper 15 as wrapped on an infant (not shown) with two of the tabs 10 fastening the diaper after tab deployment in the manner shown in FIG. 3.

Figure 5:
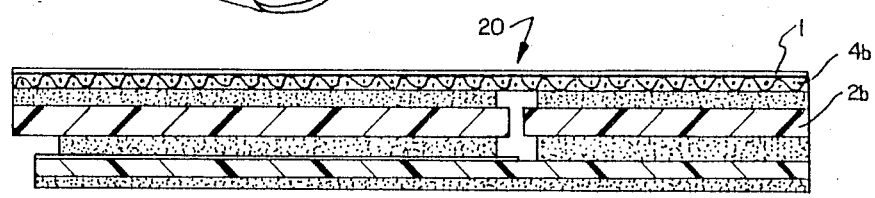
FIG. 5 shows an alternative form of the invention.

FIG. 5 shows an alternative construction which is generally similar to the previously described construction, except that the positions of the carrier layer 2b and the stretchable layer 4b have been exchanged, so that the stretchable layer becomes the top layer of the sandwich (except for release coat 1) instead of a center layer as in FIGS. 1-3.

Figure 7:
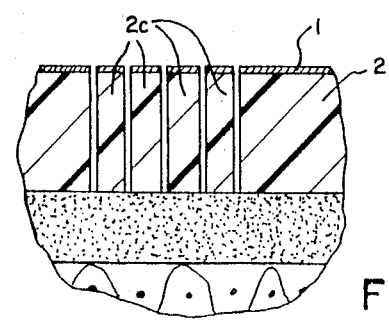
FIG. 7 is a more detailed view of the indicated portion of FIG. 6.
Figure 6:
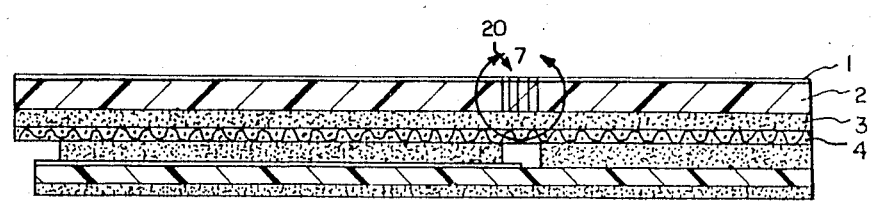
FIG. 6 shows still another alternative.

FIGS. 6 and 7 show a modification which is generally similar to the tab 10 of FIGS. 1-3, except that instead of a single slit in the non-stretchy carrier layer 2 at point 20 as in FIG. 1, several parallel slits are provided, so that between the parallel slits anti-stretch microanchors 2c are formed from small portions of the relatively non-stretchy carrier layer 2. Also, the adhesive layer 3 is not interrupted at intermediate point 20, but instead serves at this point to adhere the microanchors 2c to the extensible layer 4. This arrangement desirably tends to stablize the extensible layer 4 so as to limit and control the stretching action if it is otherwise somewhat more "loose" than is most desirable.

It should be evident that this disclosure is by way of example and that various changes may be made by adding, modifying or eliminating details without departing from the fair scope of the teaching contained in this disclosure. For example, the adhesive layer 3 need not be a pressure-sensitive adhesive, and may be a "permanent" adhesive or may be simply a heat-sealed or welded interface between layers 2 and 4 (interrupted at location 20).

Also by way of example, the invention can be used in a construction which provides a separable section that is left behind on that part of the diaper from which the tab is peeled when the diaper is opened after fastening, thus providing a "landing" or "target" for improving the reclosability of the diaper, as shown in U.S. Pat. No. 4,020,842 of common assignee.

The invention can also be used in other applications where there is need for tab fasteners of the extensible type, such as surgical drapes, surgical gowns, disposable garments, sheets, cartons, envelopes or the like.

The invention is therefore not limited to particular details of this disclosure except to the extent that the following claims are necessarily so limited.

What is claimed is:

1. A tab fastener for disposable diapers or other tab-fastened articles, said tab fastener having length, width, and thickness directions, the tab fastener comprising, with respect to its lengthwise direction, terminal segments and a central segment between the terminal segments, the tab fastener comprising, with respect to its thickness direction, inner layer means and outer layer means, said inner layer means at said terminal segments being permanently adhered to opposite sides of a side margin of the article by pressure-sensitive adhesive, said outer layer means permanently adhered to said inner layer means at a first of said terminal segments and being releasably adhered thereto at the second of said terminal segments, said inner layer means being nonextensible at least at said central segment, said nonextensibility of said inner layer means being imparted to said outer layer means when said inner and outer layer means are adhered at said second terminal segment, said outer layer means being extensible at least at said central segment upon release from said inner layer means at said second terminal segment, whereby prior to said release said inner layer means contributes to stabilizing said tab fastener against premature elongation, the outer layer means presenting a uniform outer face that is of the same material and is substantially uniformly supported by underlying layers throughout the terminal and central segments, the uniformity of the material and support of the face being substantially uninterrupted by the presence of a slit of negligible width in the lengthwise direction in a portion of the outer layer means, the face being provided with a release surface that is releasable from the pressuresensitive adhesive whereby the tab is adapted to be formed of stock material that is capable of being self-wound without significant voids.

2. A tab fastener as in claim 1 in which the extensibility of the outer layer means is concentrated at said central segment.

3. A tab fastener as in claim 2 in which the outer layer means includes a layer of extensible material and a layer of nonextensible material adhered to said layer of extensible material at said first and second terminal segments but not adhered to said layer of extensible material at at least a portion of said central segment.

4. A tab fastener as in claim 3 in which said layer of nonextensible material is on the outer side of said layer of extensible material.

5. A tab fastener as in claim 3 in which said layer of nonextensible material is on the inner side of said layer of extensible material.

6. A tab fastener as in claim 3 in which said outer layer means at said central segment includes individual microanchors formed or slit from portions of said layer of nonextensible material and adhered to said layer of extensible material.

7. A tab fastener as in claim 1 in which said releasable adherence of said outer layer to said inner layer is established by a release coat having an active face extending only partly along the length of the tab.

8. A disposable diaper having at least one tab fastener at a side margin of the diaper, the tab fastener having length, width, and thickness directions, the tab fastener comprising, with respect to its lengthwise direction, terminal segments and a central segment between the terminal segments, the tab fastener comprising, with respect to its thickness direction, inner layer means and outer layer means, said inner layer means at said terminal segments being permanently adhered to opposite sides of said diaper side margin by pressure-sensitive adhesive, said outer layer means being permanently adhered to said inner layer means at a first of said terminal segments and being releasably adhered thereto at the second of said terminal segments, said inner layer means being nonexensible at least at said central segment, said nonextensibility of said inner layer means being imparted to said outer layer means when said inner and outer layer means are adhered at said second terminal segment, said outer layer means being exensible at least at said central segment upon release from said inner layer means at said second terminal segment, whereby prior to said release said inner layer means contributes to stabilizing said tab fastener against premature elongation, the outer layer means presenting a uniform outer face that is of the same material and is substantially uniformly supported by underlying layers throughout the terminal and central segments, the uniformity of the material and support of the face being substantially uninterrupted by the presence of a slit of negligible width in said lengthwise direction in a portion of the outer layer means, the face being provided with a release surface that is releasable from the pressuresensitive adhesive whereby the tab is adapted to be formed from stock material that is capable of being self-wound without significant voids.

* * * * *